United States Patent [19]

Young

[11] Patent Number: 5,248,841
[45] Date of Patent: Sep. 28, 1993

[54] HYDROCARBON CONVERSION WITH ZSM-22 ZEOLITE

[75] Inventor: L. Brewster Young, Skillman, N.J.

[73] Assignee: Mobil Oil Corporation, Fairfax, Va.

[21] Appl. No.: 373,453

[22] Filed: Apr. 30, 1982

[51] Int. Cl.$^5$ ............................ C07C 5/27; C07C 2/66
[52] U.S. Cl. ................................ 585/467; 585/475; 585/486
[58] Field of Search ............... 585/475, 467, 486

[56] References Cited

U.S. PATENT DOCUMENTS

| | | | |
|---|---|---|---|
| Re. 29,948 | 3/1979 | Dwyer et al. | 208/110 |
| 4,049,738 | 9/1977 | Young | 585/467 |
| 4,117,026 | 9/1978 | Haag et al. | 585/475 |
| 4,139,600 | 3/1979 | Rollmann et al. | 423/329 |
| 4,146,584 | 3/1979 | Rollman | 585/467 |
| 4,181,811 | 1/1980 | Young | 585/486 |
| 4,288,647 | 9/1981 | Chu | 585/475 |
| 4,329,533 | 5/1982 | Chu | 585/475 |
| 4,481,177 | 11/1984 | Valyocsik | 423/329 |
| 4,556,477 | 12/1985 | Dwyer | 208/111 |
| 4,574,043 | 3/1986 | Chester et al. | 208/111 |
| 4,605,488 | 8/1986 | Chester et al. | 208/111 |
| 4,717,465 | 1/1988 | Chen et al. | 208/59 |
| 4,783,555 | 11/1988 | Atkins | 502/77 |
| 4,810,357 | 3/1989 | Chester et al. | 208/97 |
| 4,814,543 | 3/1989 | Chen et al. | 585/739 |
| 4,902,406 | 2/1990 | Valyocsik | 208/118 |
| 4,919,788 | 4/1990 | Chen et al. | 208/49 |
| 5,063,038 | 11/1991 | Kirker et al. | 502/77 |
| 5,135,638 | 8/1992 | Miller | 585/739 |
| 5,137,194 | 10/1992 | Rahmim et al. | 585/671 |

FOREIGN PATENT DOCUMENTS 0055045 6/1982 European Pat. Off.
0057049 8/1982 European Pat. Off.

OTHER PUBLICATIONS

Parker et al., "Synthesis and Some Properties of Two Novel Zeolites, KZ-1 and KZ-2" Zeolites, 1983, vol. 3, Jan., pp. 8–11.

*Primary Examiner*—Asok Pal
*Attorney, Agent, or Firm*—Alexander J. McKillop; Dennis P. Santini; Edward F. Kenehan, Jr.

[57] ABSTRACT

Alkylated aromatic compounds, either alone or in a mixture with an alkylating agent, are disproportionated, alkylated or transalkylated in the presence of a ZSM-22 zeolite. The products of the reactions contain the amounts of the para-isomer which are in excess of the equilibrium amounts of such isomer.

Alternatively, 1,2-disubstituted, 1,3-disubstituted and/or 1,4-disubstituted aromatic compounds are contacted with the ZSM-22 zeolite under cracking conditions to selectively crack the 1,4-disubstituted isomer.

25 Claims, No Drawings

HYDROCARBON CONVERSION WITH ZSM-22 ZEOLITE

BACKGROUND OF THE INVENTION

1. Field of the Invention

This invention relates to the use of ZSM-22 zeolite in aromatic hydrocarbon conversion reactions which produce dialkylbenzene compound product mixtures wherein the 1,4-dialkylbenzene or para isomer content is substantially in excess of its normal equilibrium concentration.

2. Description of Related Art

The disproportionation of aromatic hydrocarbons in the presence of zeolite catalysts has been described by Grandio et al. in the OIL AND GAS JOLRNAL, Vol. 69, No. 48(1971).

U.S. Pat. Nos. 3,126,422; 3,413,374; 3,598,878; 3,598,879 and 3,607,961 show vapor-phase disproportionation of toluene over various catalysts.

In these prior art processes, the dimethylbenzene product produced has the equilibrium composition of approximately 24 percent of 1,4-, 54 percent of 1,3- and 22 percent of 1,2-isomer. Of the dimethylbenzene isomers, 1,3-dimethylbenzene is normally the least desired product, with 1,2- and 1,4-dimethylbenzene being the more useful products. 1,4-Dimethylbenzene is of particular value, being useful in the manufacture of terephthalic acid which is an intermediate in the manufacture of synthetic fibers, such as "Dacron". Mixtures of dimethylbenzene isomers, either alone or in further admixture with ethylbenzene, have previously been separated by expensive super-fractionation and multistage refrigeration steps. Such process, as will be realized, involves high operation costs and has a limited yield.

Various modified zeolite catalysts have been developed to alkylate or disproportionate toluene with a greater or lesser degree of selectivity to 1,4-dimethylbenzene isomer. Hence, U.S. Pat. Nos. 3,972,832, 4,034,053, 4,128,592 and 4,137,195 disclose particular zeolite catalysts which have been treated with compounds of phosphorus and/or magnesium. Boron-containing zeolites are disclosed in U.S. Pat. No. 4,067,920 and antimony-containing zeolites in U.S. Pat. No. 3,979,472. Similarly, U.S. Pat. Nos. 3,965,208 and 4,117,026 disclose other modified zeolites useful for shape selective reactions. It is also known to incorporate various metals into zeolite catalysts by means of ion exchange.

The separation of disubstituted meta or ortho isomers from para disubstituted aromatic compounds is also a necessary but difficult step in the production of meta or ortho isomers. The differences in boiling points of some disubstituted aromatic compounds are so small that the use of distillation columns to separate the isomers is often commercially unfeasible. For example, the boiling point, at atmospheric pressure, of 1-isopropyl-2-methylbenzene (ortho-cymene) is 178.3° C., while that of 1-isopropyl-4-methylbenzene (para-cymene) is 177.1° C. Accordingly, in the past techniques other than fractional distillation were used to separate the para-isomer from the mixture thereof with the ortho- and meta-isomers. For example, Young, U.S. Pat. No. 4,181,811, discloses a process for selectively cracking, in the presence of a catalyst, e.g., ZSM-5 zeolite, 1,4-disubstituted aromatic compounds from a mixture thereof with 1,2-disubstituted aromatic compounds.

SUMMARY OF THE INVENTION

In accordance with the present invention, substituted aromatic compounds are converted in the presence of the ZSM-22 zeolite, under conversion conditions, to yield a product in which the content of 1,4-disubstituted (para)aromatic compounds is increased as compared to the content thereof in an equilibrium mixture of ortho-, meta- and para-isomers. In the process of this invention, an alkylated aromatic compound, either alone or in admixture with a suitable alkylating agent, such as methanol or ethylene, is contacted with the ZSM-22 zeolite, discussed in detail below, under suitable conversion conditions to effect disproportionation or transalkylation of alkylbenzene compounds or alkylation of aromatic compounds to selectively produce the 1,4-dialkylbenzene or para-dialkylbenzene isomer in excess of its normal equilibrium concentration.

In an alternative embodiment, mixtures of 1,2-disubstituted, 1,3-disubstituted and 1,4-disubstituted aromatic compounds are contacted with the ZSM-22 zeolite under cracking conditions to selectively react (dealkylate or crack) the 1,4-disubstituted isomer to yield products with significantly lower boiling points. The 1,4-disubstituted aromatic compounds are preferentially dealkylated while the 1,2- and the 1,3-disubstituted compounds proceed through the reaction substantially unchanged.

The ZSM-22 crystalline zeolite catalysts utilized herein comprise zeolite materials having a silica to alumina ratio of at least about 20 and a constraint index of about 2.6 at 800° F. Such catalyst compositions may be modified prior to catalytic use to replace the original cations therein with other ions using conventional ion exchange techniques. The replacing ions introduced to replace the original cations may be any that are desired so long as they can pass through the channels within the zeolite crystals. Suitable replacing ions are those of hydrogen, rare earth metals, metals of Groups IB, IIA, IIB, IIIA, IIIB, IVA, IVB and VIII of the Periodic Table of Elements.

Such catalysts can be employed for the alkylation of aromatic compounds to realize selective production of the 1,4-dialkylbenzene isomer in preference to the 1,2- and 1,3- isomers thereof. Especially preferred processes involve the selective production of 1,4-dimethylbenzene from toluene and methanol and 1-ethyl-4-methylbenzene from toluene and ethylene.

Such catalysts can also be employed to realize the selective disproportionation or transalkylation of alkylbenzene and polyalkylbenzene compounds in the presence of the disclosed catalysts, thereby yielding 1,4-disubstituted benzenes in excess of their normal equilibrium concentration. For example, under appropriate conditions of temperature and pressure, toluene will disproportionate in the presence of these catalysts to produce benzene and dimethylbenzenes mixture enriched in the desirable 1,4-isomer.

DETAILED DESCRIPTION OF THE INVENTION

The ZSM-22 zeolite used in the invention can be suitably prepared from a reaction mixture containing a source of silica, an alkane diamine, an alkali metal oxide or an alkaline earth metal oxide, e.g., sodium, potassium, cesium, calcium or strontium, water, and alumina, and having a composition, in terms of mole ratios of oxides, falling within the following ratios:

| Reactants | Broad | Preferred |
|---|---|---|
| $SiO_2/Al_2O_3 =$ | 20 to $\infty$ | 30 to 1000 |
| $H_2O/SiO_2 =$ | 10 to 100 | 20 to 60 |
| $OH^-/SiO_2 =$ | 0 to 0.3 | 0.1 to 0.2 |
| $M^+/SiO_2 =$ | 0 to 2.0 | 0.1 to 1.0 |
| $RN/SiO_2 =$ | 0.01 to 2.0 | 0.05 to 1.0 | wherein RN is a functional group of $C_2$-$C_{12}$ alkane diamine of the type $H_2N-(CH_2)_n-NH_2$ (abbreviated $C_nDN$), n=2 to 12, and preferably is 5 to 8, and M is an alkali metal or an alkaline earth metal and maintaining the mixture at crystallization temperature until crystals of the ZSM-22 zeolite are formed. Thereafter, the crystals are separated from the liquid by any conventional means, washed and recovered.

Crystallization can be carried out at either static or stirred conditions in a reactor vessel, e.g., a polypropylene jar, teflon lined or stainless steel autoclaves, at 80° C. (176° F.) to about 180° C. (356° F.) for about 6 hours to 150 days. Thereafter, the crystals are separated from the liquid and recovered. The composition can be prepared utilizing materials which supply the appropriate oxide. Such materials include aluminates, alumina, silicates, sodium silicate, silica hydrosol, silica gel, silicic acid, sodium, potassium or cesium hydroxide, and an alkane diamine. Suitable diamines are, e.g., ethanediamine, propanediamine, butanediamine, pentanediamine, hexanediamine, heptanediamine, octanediamine, nonanediamine, decanediamine, undecanediamine, duodecanediamine. Of these diamines, however, ethanediamine, propanediamine, and butanediamine, do not always produce desired results. The reaction mixture can be prepared either batchwise or continuously. Crystal size and crystallization time of the new crystalline material will vary with the nature of the reaction mixture employed and the crystallization conditions.

As set forth above, the ZSM-22 zeolite can be prepared at a relatively wide range of $SiO_2/AL_2O_3$ ratios of about 20 to about infinity ($\infty$). However, it has been found that larger alkali metal cations, e.g., $K^+$ and $Cs^+$, are preferably used at the $SiO_2/Al_2O_3$ ratios of about 20 to about 90 to obtain ZSM-22 crystals substantially free of impurities or other zeolites. The potassium ($K^+$) cation is preferred at such low $SiO_2/AL_2O_3$ ratios because cesium (Cs) appears to decrease the reaction rate. At the $SiO_2/AL_2O_3$ ratios of about 90 or above, smaller cations, e.g., sodium ($Na^+$) cations, are preferably used to produce substantially 100 percent crystalline ZSM-22.

A process for making the ZSM-22 zeolite is described in detail in a commonly-assigned application of E. W. Valyocsik, U.S. application Ser. No. 373,452, filed Apr. 30, 1982, now abandoned the entire contents of which are incorporated herein by reference.

The highly siliceous ZSM-22 zeolite comprises crystalline, three-dimensional continuous framework silicon-containing structures or crystals which result when all the oxygen atoms in the tetrahedra are mutually shared between tetrahedral atoms of silicon or aluminum, and which can exist with a network of mostly $SiO_2$, i.e., exclusive of any intracrystalline cations. Similar crystals form building blocks of materials, such as quartz, cristobalite and a long list of zeolite structures such as ZSM-5, ZSM-11, ZSM-12, ZSM-23, ZSM-35, ZSM-38, ZSM-48 (described in European Patent Application Number 80,300,463 published Sept. 3, 1980 as Publication Number 0,015,132, the entire content of which is incorporated herein by reference), mordenite and perhaps even faujasite. Not all zeolite structures are known to exist at this time in predominantly $SiO_2$-containing compositions—so the above class of materials does not presently include some zeolites, such as zeolite A.

The ZSM-22 zeolite also may contain a relatively minor amount of $Al_2O_3$ and therefore can produce a product with a $SiO_2$ to $Al_2O_3$ ratio of about 20 to about $\infty$. In the as-synthesized form, the ZSM-22 has a calculated composition, in terms of moles of oxides, after dehydration, per 100 moles of silica, as follows:

$$(0.02 \text{ to } 10)RN:(0 \text{ to } 2)M_{2/n}O:(0 \text{ to } 5)Al_2O_3:100SiO_2$$

wherein RN is a functional group of $C_2$-$C_{12}$ alkane diamine and M is an alkali metal or an alkaline earth metal having a valence n, e.g., Na, K, Cs, Li, Ca or Sr.

ZSM-22 can further be identified by its sorptive characteristics and its X-ray diffraction pattern. The original cations of the as-synthesized ZSM-22 may be replaced at least in part by other ions using conventional ion exchange techniques. It may be necessary to precalcine the ZSM-22 zeolite crystals prior to ion exchange. The replacing ions introduced to replace the original alkali, alkaline earth and/or organic cations may be any that are desired so long as they can pass through the channels within the zeolite crystals. Desired replacing ions are those of hydrogen, rare earth metals, metals of Groups IB, IIA, IIB, IIIA, IIIB, IVA, IVB, VIB and VIII of the Periodic Table. Among the metals, those particularly preferred are rare earth metals, manganese, zinc and those of Group VIII of the Periodic Table.

ZSM-22 zeolite described herein has a definite X-ray diffraction pattern, set forth below in Table I, which distinguishes it from other crystalline materials.

TABLE I

| Most Significant Lines of ZSM-22 | |
|---|---|
| Interplanar d-spacings (Å) | Relative Intensity |
| 10.9 ± 0.2 | M-VS |
| 8.7 ± 0.16 | W |
| 6.94 ± 0.10 | W-M |
| 5.40 ± 0.08 | W |
| 4.58 ± 0.07 | W |
| 4.36 ± 0.07 | VS |
| 3.68 ± 0.05 | VS |
| 3.62 ± 0.05 | S-VS |
| 3.47 ± 0.04 | M-S |
| 3.30 ± 0.04 | W |
| 2.74 ± 0.02 | W |
| 2.52 ± 0.02 | W |

These values were determined by standard techniques. The radiation was the K-alpha doublet of copper and a diffractometer equipped with a scintillation counter and an associated computer were used. The peak heights, I, and the positions as a function of 2 theta, where theta is the Bragg angle, were determined using algorithms on the computer associated with the spectrometer. From these, the relative intensities, 100 $I/I_o$, where $I_o$ is the intensity of the strongest line or peak, and d (obs.) the interplanar spacing in angstroms (Å), corresponding to the recorded lines, were determined. In Table I, the relative intensities are given in terms of the symbols vs=very strong, s=strong, m=medium, w=weak, etc. It should be understood that this X-ray diffraction pattern is characteristic of all the species of ZSM-22 zeolite compositions. Ion exchange of the alkali or alkaline earth metal cations with other ions results in a zeolite which reveals substantially the same X-ray diffraction pattern as that of Table I with some minor shifts in interplanar spacing and variations in relative intensity. Other minor variations can occur, depending on the silica to alumina ratio of the particular sample, as well as its degree of thermal treatment.

The ZSM-22 zeolite freely sorbs normal hexane and has a pore dimension greater than about 4 Angstroms. In addition, the structure of the zeolite must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous hydrocarbon conversions, although puckered structures exist such as TMA offretite which is a known effective zeolite. Also, such twelve-membered structures can be conceived that may be operative due to pore blockage or other causes.

Rather than attempt to judge from crystal structure whether or not a zeolite possesses the necessary constrained access, a simple determination of the "constraint index" may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tlbe. Prior to testing, the zeolite is treated with a stream of air at 1000° F. for at least 15 minutes. The zeolite is then flushed with helium and the temperature adjusted between 550° F. (288° C.) and 950° F. (510° C.) to give an overall conversion between 10 percent and 60 percent. The mixture of hydrocarbons is passed at a 1 liquid hourly space velocity (LHSV), i.e., 1 volume of liquid hydrocarbon per volume of zeolite per hour, over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Constraint Index (CI) values for some typical zeolites are:

| ZEOLITE | C.I. |
| --- | --- |
| ZSM-5 | 8.3 |
| ZSM-11 | 8.7 |
| ZSM-12 | 2 |
| ZSM-23 | 9.1 |
| ZSM-38 | 2 |
| ZSM-35 | 4.5 |
| Clinoptilolite | 3.4 |
| TMA Offretite | 3.7 |

-continued

| ZEOLITE | C.I. |
| --- | --- |
| Beta | 0.6 |
| ZSM-4 | 0.5 |
| H-Zeolon | 0.4 |
| REY | 0.4 |
| Amorphous Silica-Alumina (non-zeolite) | 0.6 |
| Erionite | 38 |

It is to be realized that the above constraint index values typically characterize the specified zeolites but that these are the cumulative result of several variables used in determination and calculation thereof. Thus, for a given zeolite depending on the temperature employed within the aforenoted range of 550° F. to 950° F., with accompanying conversion between 10 percent and 60 percent, the constraint index may vary within the indicated approximate range of 1 to 12. Likewise, other variables such as the crystal size of the zeolite, the presence of possible occluded contaminants and binders intimately combined with the zeolite, may affect the constraint index. It will accordingly be understood by those skilled in the art that the constraint index, as utilized herein, while affording a highly useful means for characterizing the zeolites of interest, is an approximation, taking into consideration the manner of its determination, with probability, in some instances, of compounding variable extremes:

While the above experimental procedure will enable one to achieve the desired overall conversion of 10 to 60 percent for most catalyst samples and represents preferred conditions, it may occasionally be necessary to use somewhat more severe conditions for samples of very low activity, such as those having a very high silica to alumina mole ratio. In those instances, a temperature of up to about 1000° F. and a liquid hourly space velocity of less than one, such as 0.1 or less, can be employed in order to achieve a minimum total conversion of about 10 percent.

The particular class of zeolites to which the ZSM-22 zeolite belongs is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re. 29,948. The entire contents of both of these patents are incorporated herein by reference.

ZSM-11 is described in U.S. Pat. No. 3,709,979, the entire content of which is incorporated herein by reference.

ZSM-12 is described in U.S. Pat. No. 3,832,449, the entire content of which is incorporated herein by reference.

ZSM-23 is described in U.S. Pat. No. 4,076,842, the entire content of which is incorporated herein by reference.

ZSM-35 is described in U.S. Pat. No. 4,016,245, the entire content of which is incorporated herein by reference.

ZSM-38 is described in U.S. Pat. No. 4,046,859, the entire content of which is incorporated herein by reference.

ZSM-48 is described in European Patent Application Number 800,300,463 published Sept. 3, 1980, as Publication Number 0,015,132, the entire content of which is incorporated herein by reference.

Preliminary data indicates that the ZSM-22 zeolite has an orthorhombic noncentral structure consisting substantially of 5 and 6-member rings which form a substantially unidirectional 10-ring channel system. Four member rings appear to be completely absent from the structure, which may explain, at least to some extent, the relatively high thermal stability of ZSM-22. (A sample of ZSM-22 was found to be thermally stable after heating at 550° C. in air for 20 hours, and substantially steam stable, after the treatment at 920° F.—about 493° C. - for 5 hours in 1 atm saturated steam.) The ZSM-22 crystalline structure appears to be similar to zeolites of the ZSM-5 family, particularly ZSM-5, ZSM-11, ZSM-23, and ZSM-35. Accordingly, its performance characteristic may be similar to those of the aforementioned zeolites of the ZSM-5 family. Preliminary data, however, does not completely support this hypothesis. For example, the alpha activity, set forth in Table II, of ZSM-22 samples is less than that predicted for the ZSM-5 zeolite of equivalent SiO /AL 0 ratios. Without wishing to be bound by any theory of operability, it is possible that trace amounts of the potassium cation (K+) strategically located within the unidimensional channels may account for the reduced activity of the zeolite. Extractions of ZSM-22 samples with hydrochloric acid (HCl) to reduce the K+ level in the zeolite may be effective in improving $\alpha$ activity.

TABLE II

Comparison of Activities for ZSM-22 and ZSM-5

| Form | Wt % K Present | $\alpha$-value Observed | (expected) |
|---|---|---|---|
| As-synthesized | 2.3 | — | (—) |
| TMA-exchanged[a] | 0.41 | 35 | ($\alpha$ = 130)[c] |
| NH4-exchanged[b] | 0.04 | 61 | ($\alpha$ = 130)[c] |

[a]98° C., stirred 6 hrs. in 0.5 $\underline{N}$ tetramethyl ammonium bromide (TMABr).
[b]98° C., stirred 6 hrs. in 1.0 $\underline{N}$ NH4NO3.
[c]$\alpha$-value expected for ZSM-5 of equivalent SiO2/Al2O3 ratio.

The alpha-test ($\alpha$-test) is an indication of the relative catalytic cracking activity of the catalyst compared to a standard catalyst. The value of $\alpha$ is the relative rate constant (rate of n-hexane conversion per unit volume of oxides composition per unit time). It is based on the activity of highly active silica-alumina cracking catalyst taken as $\alpha = 1$.

The $\alpha$-test is further described in a letter to the editor, entitled "Superactive Crystalline Alumina-Silicate Hydrocarbon Cracking Catalysts", by P. B. Weisz and J. N. Miale, *Journal of Catalysis*, Vol. 4, pp. 527-529 (Aug. 1965) and in U.S. Pat. No. 3,354,078, the entire contents of both of which are incorporated herein by reference.

The sorption of hydrocarbons by ZSM-22 has also been surveyed and the results are summarized in Table III. Sorption capacities for n-hexane (normal hexane), cyclohexane, and water are about 4 percent by weight, or about one third that of ZSM-5. Without wishing to be bound by any theory of operability, it is thought that the reduced sorption capacity may be due to the unidimensional channel system of ZSM-22, but residual K+ within the channels may also contribute to the relatively low sorption capacities. Cyclohexane and o-xylene sorption is relatively slow, making it difficult to determine equilibrium capacities.

TABLE III

| | | ZSM-22 Sorption Data | | | |
|---|---|---|---|---|---|
| | | Sorptions (wt %)[a] | | | |
| Sample | Form | n-hexane | 3-methyl-pentane | Cyclo-hexane[c] | H2O | o-xylene[b] |
| 1 | Hydrogen | 3.9 | — | 2.8 | — | — |
| 2 | (H) H | 4.2 | 3.9 | 1.1 | — | 2 |
| 3 | H | 4.1 | — | 3.3 | 4.7 | — |
| 4 | as-synthesized | 3.4 | — | — | — | — |

[a]Hydrocarbons: pressure = 20 mm, temperature = 25° C.; water - pressure = 12 mm, temperature = 25° C.
[b]pressure = 3.7 mm, temperature = 120° C.
[c]slow tailing sorption, nonequilibrium values.

Preliminary results also indicate that ZSM-22 is para-selective in its catalytic reactions. The ZSM-22 zeolite, as synthesized, tends to crystallize as agglomerates of elongated crystals having the size of about 0.5 to about 2.0 microns ($\mu$). Ballmilling fractures these crystals into smaller size crystallites (about $0.1/\mu$) without significant loss of crystallinity. The zeolite can be shaped into a wide variety of particle sizes. Generally speaking, the particles can be in the form of a powder, a granule, or a molded product, such as an extrudate having particle size sufficient to pass through a 2 mesh (Tyler) screen and be retained on a 400 mesh (Tyler) screen. In cases where the catalyst is molded, such as by extrusion, the crystals can be extruded before drying or partially dried and then extruded.

While synthetic ZSM-22 zeolites may be used in a wide variety of hydrocarbon conversion reactions, they are notably useful in the processes of polymerization, aromatization and cracking. Other hydrocarbon conversion processes for which ZSM-22 may be utilized in one or more of its active forms include, for example, hydrocracking and converting light aliphatics to aromatics. A process for converting light aliphatics to aromatics over a ZSM-5 type zeolite is disclosed in U.S. Pat. No. 3,760,024, the entire contents of which are incorporated herein by reference.

Employing a catalytically active form of the ZSM-22 catalyst for polymerization of olefins containing liquid or gaseous charge stocks, such charge stocks can be polymerized at temperatures between 550° and 850° F. (about 290° and 450° C.) at an hourly space velocity of between 0.5 and 50 WHSV (weight hourly space velocity) and a pressure of between 0.1 and 800 psig. In employing the ZSM-22 catalyst for aromatization of gaseous or liquid charge stocks which may be olefinic or paraffinic, with or without aromatics present, such stocks can be aromatized at temperatures of between 800 and 1200° F. (about 430° and 650° C.), pressures of 1 to 10 atmospheres and space velocities of between 0.1 and 10 weight hourly space velocity (WHSV).

Synthetic ZSM-22 zeolites can be used either in the organic nitrogen-containing and alkali metal-containing form, the alkali metal form and hydrogen form or another univalent or multivalent cationic form. The as-synthesized zeolite may be conveniently converted into the hydrogen, the univalent or multivalent cationic forms by base exchanging the zeolite to remove the sodium cations by such ions as hydrogen (from acids), ammonium, alkylammonium and arylammonium, including $RNH_3$, $R_3NH^+$, $R_2NH_2^+$ and $R_4N^+$ where R is alkyl or aryl, provided that steric hindrance does not prevent the cations from entering the cage and cavity structure of the ZSM-22 type crystalline zeolite. The hydrogen form of the zeolite, useful in such hydrocarbon conversion processes as isomerization of polysubstituted alkyl aromatics and disproportionation of alkyl aromatics, is prepared, for example, by base exchanging the sodium form with, e.g., ammonium chloride or hydroxide, whereby the ammonium ion is substituted for the sodium ion. The composition is then calcined, at a temperature of, e.g., 1000° F. (about 540° C.), causing evolution of ammonia and retention of the hydrogen proton in the composition. Other replacing cations include cations of the metals of the Periodic Table, particularly metals other than sodium, most preferably metals of Group IIA, e.g., zinc, and Groups IIIA, IVA, IB, IIB, IIIB, IVB, VIB and Group VIII of the Periodic Table, and rare earth metals and manganese.

Ion exchange of the zeolite can be accomplished conventionally, e.g., by packing the zeolite into a series of vertical fixed bed columns and successively passing through the beds a water solution of a solable salt of the cation to be introduced into the zeolite, and then changing the flow from the first bed to a succeeding one as the zeolite in the first bed becomes ion exchanged to the desired extent. Aqueous solutions of mixtures of materials to replace the sodium can be employed. For instance, if desired, one can exchange the sodium with a solution containing a number of rare earth metals suitably in the chloride form. Thus, a rare earth chloride solution commercially available can be used to replace substantially all of the sodium in the as synthesized ZSM-22 zeolite. One such commercially available rare earth chloride solution contains chlorides of a rare earth mixture having the relative composition: cerium (as $CeO_2$) 48 percent by weight, lanthanum (as $La_2O_3$) 24 percent by weight, praseodymium (as $Pr_6O_{11}$) 5 percent by weight, neodymium (as $Nd_2O_3$) 17 percent by weight, samarium (as $SM_2O_3$) 3 percent by weight, gadolinium (as $Gd_2O_3$) 2 percent by weight, and other rare earth oxides 0.8 percent by weight. Didymium chloride, which can also be used as an exchanging solution, is also a mixture of rare earth chlorides, but having a lower cerium content. It consists of the following rare earth metals determined as oxides: lanthanum 45-65 percent by weight, cerium 1-2 percent by weight, praseodymium 9-10 percent by weight, neodymium 32-33 percent by weight, samarium 5-7 percent by weight, gadolinium 3-4 percent by weight, yttrium 0.4 percent by weight, and other rare earth metals 1-2 percent by weight. It is to be understood that other mixtures of rare earth metals are also applicable for the preparation of the novel compositions of this invention, although lanthanum, neodymium, praseodymium, samarium and gadolinium as well as mixtures of rare earth cations containing a predominant amount of one or more of the above cations are preferred.

Base exchange with various metallic and non-metallic cations can be carried out according to the procedures described in U.S. Pat. Nos. 3,140,251, 3,140,252 and 3,140,253, the entire contents of which are incorporated herein by reference.

The ZSM-22 crystal can also be used as a catalyst in intimate combination with a hydrogenating component, such as tungsten, vanadium, molybdenum, rhenium, nickel, cobalt, chromium, manganese, or a noble metal, such as platinum or palladium where a hydrogenation-dehydrogenation function is desired. Such component can be exchanged into the composition, impregnated therein or physically intimately admixed therewith. Such component can be impregnated in or onto the zeolite, for example, in the case of platinum, by treating the zeolite with a solution containing a platinum metal-containing ion. Thus, suitable platinum compounds include chloro-platinic acid, platinous chloride and various compounds containing the platinum tetrammine-platinum complex. Combinations of the aforementioned metals and methods for their introduction can also be used.

Synthetic ZSM-22 zeolite, when employed either as an absorbent or as a catalyst in a hydrocarbon conversion process, should be at least partially dehydrated. This can be accomplished by heating the zeolite to a temperature in the range of about 200° C. to about 600° C. in an inert atmosphere, such as air or nitrogen for about 1 to about 48 hours. Simple dehydration of the crystal can also be performed at lower temperatures, such as room temperature, merely by placing the ZSM-22 zeolite type crystal in a vacuum, but a longer time is required to obtain a sufficient degree of dehydration.

In the case of many catalysts, it is desired to incorporate the new crystal with another material resistant to the temperatures and other conditions employed in organic conversion processes. Such materials include active and inactive materials and synthetic or naturally occurring zeolites as well as inorganic materials, such as clays, silica and/or metal oxides. The clays, silica and/or metal oxides may be either naturally occurring or in the form of gelatinous precipitates or gels including mixtures of silica and metal oxides. The use of such additional active material in conjunction with the new ZSM-22 crystal, i.e., combined therewith, tends to improve the conversion and/or selectivity of the catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g., bentonite and kaolin, to improve the crush strength of the catalyst under commercial operating conditions. Such materials, e.g., clays or oxides, function as binders for the catalyst. It is desirable to provide a catalyst having good crush strength because in commercial use it is desirable to prevent the catalyst from breaking down into powder-like materials. These clay binders are normally employed for the purpose of improving the crush strength of the catalyst and they can be employed to perform the same function in combination with the ZSM-22 zeolite.

Naturally occurring clays which can be composited with the new zeolite include the montmorillonite and kaolin family, which families include the subbentonites, and the kaolins commonly known as Dixie, McNamee-Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the ZSM-22 zeolite can be composited with a porous matrix material, such as silica-alumina, silica-magnesia, silica-zirconia, silica-thoria, silica-beryllia, silica-titania, as well as ternary compositions, such as silica-alumina-thoria, silica-alumina-zirconia, silica-alumina-magnesia and silica-magnesia-zirconia. The relative proportions of finely divided crystalline material and inorganic oxide gel matrix vary widely, with the crystal content ranging from about 1 to about 90 percent by weight.

Alkylation of aromatic compounds in the presence of the above-described ZSM-22 catalysts can be effected by contact of the aromatic compound with an alkylating agent. A particularly preferred embodiment involves the alkylation of toluene wherein the alkylating agents employed comprise methanol or other well known methylating agents or ethylene. The reaction is carried out at a temperature of between about 250° C. and about 750° C., preferably between about 300° C. and 650° C., and at liquid hourly space velocity (LHSV) of 0.1 to 1000. At higher temperatures, the ZSM-22 zeolites of high silica/alumina ratio are preferred. The reaction generally takes place at atmospheric pressure, but pressures within the approximate range of $10^4 N/m^2$ to $10^7 N/m^2$ (0.1-100 atmospheres) may be employed.

Some non-limiting examples of suitable alkylating agents include olefins of 2 to 12 carbon atoms, such as, for example, ethylene, propylene, butene, decene and dodecene, as well as formaldehyde, alkyl halides and alcohols, the alkyl portion thereof having from 1 to 16 carbon atoms. Numerous other aliphatic compounds having at least one reactive alkyl radical may be utilized as alkylating agents.

Aromatic compounds which may be selectively alkylated as described herein include any alkylatable substituted or nonsubstituted aromatic hydrocarbon. Among substituted aromatic hydrocarbons, particularly preferred are monosubstituted aromatic hydrocarbons wherein the substituent is an alkyl of 1 to 10 carbon atoms. Suitable alkylatable aromatic hydrocarbons are, for example, benzene, ethyl-benzene, toluene, dimethylbenzenes, diethylbenzenes, methylethyl-benzenes, propylbenzene, isopropylbenzene, isopropylmethyl-benzenes, butylbenzene, or substantially any mono- or disubstituted benzenes which are alkylatable in the 4-position of the aromatic ring.

The molar ratio of alkylating agent to aromatic compound is generally between about 0.05 and about 5. For instance, when methanol is employed as the methylating agent and toluene is the aromatic, a suitable molar ratio of methanol to toluene has been found to be approximately 1-0.1 moles of methanol per mole of toluene. Reaction is suitably accomplished utilizing a feed weight hourly space velocity (WHSV) of between about 0.1 and about 1000, and preferably between about 1 and about 200. The reaction product, consisting predominantly of the 1,4-dialkyl isomer, e.g., 1-4,dimethylbenzene, 1-ethyl-4-methylbenzene (para-ethyltoluene), or a mixture of the 1,4- and 1,2-isomers together with comparatively smaller amounts of 1,3-dialkylbenzene isomer, may be separated by any suitable means. Such means may include, for example, passing the reaction product stream through a water condenser and subsequently passing the organic phase through a column in which chromatographic separation of the aromatic isomers is accomplished.

When transalkylation is to be accomplished, transalkylating agents are alkyl or polyalkyl aromatic hydrocarbons wherein alkyl may be composed of from 1 to about 5 carbon atoms, such as, for example, toluene, xylene, trimethylbenzene, triethylbenzene, dimethylethylbenzene, ethylbenzene, diethylbenzene, ethyltoluene.

Another aspect of this invention involves the selective disproportionation of alkylated aromatic compounds to produce dialkylbenzenes wherein the yield of 114-dialkyl isomer is in excess of the normal equilibrium concentration. In this context, it should be noted that disproportionation is a special case of transalkylation in which the alkylatable hydrocarbon and the transalkylating agent are the same compound, for example, when toluene serves as the donor and acceptor of a transferred methyl group to produce benzene and xylene.

The transalkylation and disproportionation reactions are carried out by contacting the reactants with the above-described zeolite catalyst at a temperature of between about 350° C. and 750° C. at a pressure of between about atmospheric ($10^5 N/m^2$) and about 100 atmospheres ($10^7 N/m^2$). The reactant feed WHSV will normally fall within the range of about 0.1 to about 50. Preferred alkylated aromatic compounds suitable for utilization in the disproportionation embodiment comprise toluene, ethylbenzene, propylbenzene or substantially any monosubstituted alkylbenzene. These aromatic compounds are selectively converted to, respectively, 1,4-dimethylbenzene, 1,4-diethylbenzene, 1,4-dipropylbenzene, or other 1,4-dialkylbenzene, as appropriate, with benzene being a primary side product in each instance. The product is recovered from the reactor effluent by any conventional means, such as distillation, to remove the desired products of benzene and dialkylbenzene, and any unreacted aromatic component is recycled for further reaction.

In an alternative embodiment of the invention, mixtures comprising positional isomers of one or more disubstituted aromatic compounds, said isomers being the 1,2-isomer and/or the 1,3-isomer with at least some of the 1,4-isomer present, are brought into contact, under cracking or transalkylation conditions, with a bed comprising a particulate catalyst containing a crystalline ZSM-22 zeolite. The 1,4-disubstituted isomer is selectively dealkylated or transalkylated to facilitate subsequent removal from the mixture, in its entirety or at least in substantial part, by carrying out the process at temperatures of between about 150° C. and 800° C., pressures of between about $10^4$ and about $10^7 N/m^2$ (about 0.1 to 100 atmospheres), and a feed weight hourly space velocity (WHSV) of between about 0.1 and about 100. The latter WHSV is based upon the weight of the catalyst compositions, i.e., the total weight of active catalyst and binder therefor. It is preferred that contact between the catalyst and the disubstituted aromatic compounds be carried out at from about 250° C. to about 550° C., and at a WHSV of from about 0.2 to 50. Although the reaction normally takes place at atmospheric pressure (i.e. $10^5 N/m^2$) the preferred pressure range extends from about $2 \times 10^4$ to about $2.5 \times 10^6 N/m^2$ (0.2 to 25 atmospheres). The 1,2-disubstituted aromatic compounds and/or the 1,3-disubstituted aromatics, singly or together as desired, may subsequently be separated from the reaction effluent by any suitable means.

Particularly preferred disubstituted aromatic compounds used in this embodiment are the positional isomers of cymene i.e., 1-isopropyl-2-methylbenzene (ortho-cymene), 1-isopropyl-3-methylbenzene (meta-cymene) and 1-isopropyl-4-methylbenzene (para-cymene). For example, in the cracking reaction of para- and meta-cymene in the presence of the ZSM-22 zeolite, the para-cymene is preferentially cracked to produce predominantly toluene, while the amount of the meta-cymene remains substantially unchanged.

The hydrocarbon conversion processes described herein may be carried out as a batch type, semi-continuous or continuous operation utilizing a fixed or moving bed catalyst system. The catalyst, after use in a moving bed reactor, is conducted to a regeneration zone wherein coke is burned from the catalyst in an oxygen-containing atmosphere, e.g., air, at an elevated temperature, after which the regenerated catalyst is recycled to the conversion zone for further contact with the charge stock. In a fixed bed reactor, regeneration is carried out in a conventional manner where an inert gas containing a small amount of oxygen (0.5-2 percent) is used to burn the coke in a controlled manner so as to limit the temperature to a maximum of around 500°-550° C.

The process may be carried out in a system wherein the substituted or non-substituted aromatic compounds are in either the liquid or the vapor state. The feed stream for the process of this invention may contain other inert materials as diluents or solvents. Suitable diluents include, but are not limited to: methane, nitrogen, propane, hexane, steam and carbon dioxide.

The following examples illustrate certain specific embodiments of the hereindisclosed invention. These examples should not, however, be construed as limiting the scope of the invention as there are many variations which may be made thereon without departing from the spirit of the disclosed invention as will be apparent to those skilled in the art.

EXAMPLE 1

Synthesis of ZSM-22 having product $SiO_2/Al_2O_3$ molar ratio of 74

$Al_2(SO_4)_3.16H_2O$, the source of alumina, potassium hydroxide, water and octanediamine, $H_2N-(CH_2)_8-NH_2$, the organic promoter, RN, were mixed together and transferred to a stainless steel autoclave. Silica sol (30 percent $SiO_2$, 70 percent $H_2O$), the silica source, was added with stirring to the mixture in the autoclave. The reaction mixture composition, in mole ratios, was:

$SiO_2/Al_2O_3 = 90$ $H_2O/SiO_2 = 40$ $OH^-/SiO_2 = 0.20$ $K^+/SiO_2 = 0.30$ $RN/SiO_2 = 0.30$

The reaction mixture was stirred at 400 rpm and was maintained at 160° C. for four (4) days, at which time crystallization was completed. The crystalline solids were separated from any unreacted components by filtration and then water washed. X-ray diffraction analysis revealed that the product was 100 percent ZSM-22 zeolite. The crystals were then dried at 110° C.

The chemical composition, in moles, of the product was as follows:

$N_2O = 2.6$ $K_2O = 0.51$ $Al_2O_3 = 1.0$ $SiO_2 = 74$

The as-synthesized ZSM-22 powder was precalcined in a tube furnace in flowing nitrogen (150 ml/min) from room temperature to 550° C. at a rate of 2° C./min. When the sample reached 550° C., the nitrogen was replaced by air (also at 150 ml/min), and the sample was held at 550° C. for 24 hours at that air flow rate.

The calcined ZSM-22 powder was now $NH_4^\pm$ exchanged in 1.0N $NH_4NO_3$ solution with stirring at 80° C. for 6 hours. After exchange, the zeolite was filtered, washed with water, and dried at 110° C.

EXAMPLE 2

Synthesis of ZSM-22 having product $SiO_2/Al_2O_3$ molar ratio of 64

Solution A, containing 1.7 g $Al_2(SO_4)_3.16H_2O$, 3.9g KOH, 0.2g KCl, 10.4g 1,8-octanediamine ($C_8DN$), and 87.8g of water, was mixed with solution B, containing 48.0g silica sol (30 percent $SiO_2$) and 50.0g water, in a 300ml stainless steel autoclave. In terms of mole ratios the hydrogel had the following composition:

$SiO_2/Al_2O_3 = 90$ $H_2O/SiO_2 = 40$ $OH^-/SiO_2 = 0.20$ $K^+/SiO_2 = 0.30$ $C_8DN/SiO_2 = 0.30$

The hydrogel was reacted at 160° C. with stirring (400 rpm) at autogenous pressure for 2 days. The resultant product was filtered, washed with water, and dried at 110° C. X-ray and Scanning Electron Microscopic analysis of the product revealed 100 percent crystalline ZSM-22 with needle-like crystal morphology of 0.2-1.0μμ length.

EXAMPLE 3

Synthesis of ZSM-22 having product $SiO_2/Al_2O_3$ ratio of 52

$Al_2(SO_4)_3.16H_2O$, potassium hydroxide, water and hexanediamine, $H_2N-(CH_2)_6-NH_2$, were mixed together and transferred to a stainless steel autoclave. Silica sol (30 percent $SiO_2$, 70 percent $H_2O$) was added with stirring to the mixture in the autoclave. The reaction mixture composition, in mole ratios, was:

$SiO_2/Al_2O_3 = 60$ $H_2O/SiO_2 = 40$ $OH^-/SiO_2 = 0.20$ $K^+/SiO_2 = 0.33$ $RN/SiO_2 = 0.30$

The reaction mixture was stirred at 400 rpm and it was maintained at 160° C. for 4 days, at which time the crystallization was completed. The crystalline solids were separated from any unreacted components by filtration, and then water washed. X-ray diffraction analysis revealed that the product was 100 percent ZSM-22 zeolite.

The chemical composition, in moles, of the product was:

$N_2O = 2.28$ $K_2O = 0.45$ $Al_2O_3 = 1.0$ $SiO_2 = 52$

The product was thoroughly calcined by heating at 550° C. for 15 hours.

EXAMPLE 4

Disproportionation reaction with ammonia-exchanged ZSM-22 (HZSM-22)

Three grams of ZSM-22 of Examples 1 or 3 (product $SiO_2:Al_2O_3$ mole ratio=64 or 52 respectively) were placed in a small quartz continuous-flow reactor and heated to the temperature set forth below for different runs. The pressure in the reactor was maintained at 1.0 atmosphere and the liquid hourly space velocity was as noted below. The results are summarized in Table IV.

TABLE IV

| ZSM-22 of Example | Temperature (°C.) | LHSV | Toluene Conversion (Mole %) | Distribution of Ortho (O), Meta (M) and Para (P) Isomers in Xylene Products (Mole %) | | | | | |
|---|---|---|---|---|---|---|---|---|---|
| | | | | Reaction | | | Equilibrium | | |
| | | | | O | M | P | O | M | P |
| 1 | 500 | 2.8 | 1 | 25.3 | 40.5 | 34.3 | 26 | 51.0 | 23 |
| 3 | 500 | 2.8 | 2.5 | 27.5 | 42.2 | 30.3 | | | |
| 3 | 500 | 2.8 | 2.0 | 27.2 | 41.0 | 31.8 | | | |
| 3 | 550 | 2.8 | 3.5 | 26.9 | 44.5 | 28.5 | | | |
| 3 | 550 | 2.8 | 3.5 | 26.9 | 43.9 | 29.2 | | | |
| 3 | 550 | 2.8 | 4.2 | 26.8 | 44.1 | 29.0 | | | |
| 3 | 550 | 2.8 | 3.8 | 27.6 | 42.0 | 30.3 | | | |
| 3 | 550 | 2.8 | 2.7 | 28.1 | 41.2 | 30.8 | | | |

EXAMPLE 5

Toluene Alkylation With Methanol

Alkylation) of toluene with methanol was carried out by passing a toluene/methanol mixture at 1 atmosphere, and in a molar ratio, at the temperature and LHSV conditions indicated in Table V below for individual runs. The results are also summarized below. The equilibrium distribution of the ortho-(O), meta-(M) and para-(P) xylene isomers for this reaction is: O=26; P=23; M=51.

TABLE V

| Run | ZSM-22 of Example | Toluene to Methanol Ratio (Moles) | Temperature (°C.) | LHSV | Toluene Conversion (Mole %) | Distribution of O, M, & P isomers in Xylene Products (Mole %) | | |
|---|---|---|---|---|---|---|---|---|
| | | | | | | O | M | P |
| A | 1 | 5.2 | 500 | 4.3 | 10.4 | 26 | 16 | 57 |
| B | 1 | 5.2 | 500 | 4.3 | 11.5 | 24 | 15 | 61 |
| C | 1 | 5.2 | 600 | 4.3 | 11.3 | 26 | 19 | 55 |
| D | 2 | 4.0 | 500 | 2.8 | 13.1 | 27.9 | 41.8 | 30.3 |
| E | 2 | 4.0 | 500 | 2.8 | 14.1 | 28.2 | 40.6 | 31.2 |
| F | 1 | 4.0 | 500 | 2.8 | 12.5 | 28.2 | 29.8 | 42.0 |
| G | 1 | 4.0 | 550 | 2.8 | 15.0 | 28.0 | 29.3 | 42.7 |

EXAMPLE 6

Toluene Alkylation With Ethylene

In a manner similar to that of Example 5, alkylation of toluen with ethylene was carried out by passing toluene and ethylene, at the conditions specified below for individual runs, over 3 grams of the ZSM-22 zeolite of Example 1. The results are summarized in Table VI below. The equilibrium distribution of the ortho, meta-, and para-ethyltoluene isomers of this reaction is: O=18; P=32; M=50.

TABLE VI

| Run | Toluene to Methanol Ratio (Moles) | Temperature (°C.) | LHSV | Toluene Conversion (Mole %) | Distribution of O, M, & P isomers in Xylene Products (Mole %) | | |
|---|---|---|---|---|---|---|---|
| | | | | | O | M | P |
| A | 3.9 | 450 | 2.9 | 1.9 | — | 14 | 86 |
| B | 3.9 | 550 | 2.9 | 1.5 | — | 26 | 74 |

EXAMPLE 7

Cracking of meta-/para-cymene mixture

A mixture comprising 67 weight percent of 1-isopropyl-3-methylbenzene (meta-cymene), 28 weight percent of 1-isopropyl-4-methylbenzene (para-cymene), was passed over 3 grams of ZSM-22 zeolite of Example 1, at the conditions summarized below in Table VII.

TABLE VII

| | Selective Cracking of Cymenes | | | | | |
|---|---|---|---|---|---|---|
| Catalyst: | Feedstock | ZSM-22 | ZSM-22 | ZSM-22 | ZSM-5 | ZSM-5 |
| Temperature (°C.) | — | 300 | 300 | 400 | 250 | 250 |
| LHSV (hr$^{-1}$) of hydrocarbon | — | 1.1 | 1.1 | 1.1 | 1.1 | 2.8 |
| GHSV (hr$^{-1}$) of $N_2$ | — | 0 | 660 | 660 | 0 | 0 |
| Composition: | | | | | | |

TABLE VII-continued

| | Selective Cracking of Cymenes | | | | | |
|---|---|---|---|---|---|---|
| Catalyst: | Feedstock | ZSM-22 | ZSM-22 | ZSM-22 | ZSM-5 | ZSM-5 |
| (Wt % of aromatics) | | | | | | |
| Benzene | 0.0 | 0.0 | | 0.38 | | |
| Toluene | 0.07 | 4.62 | 3.06 | 16.77 | | |
| Dimethylbenzene | 0.094 | 0.04 | 0.04 | 0.09 | | |
| | 0.048 | 0.08 | 0.06 | 0.08 | | |
| ortho-cymene | 4.50 | 4.54 | 4.56 | 4.02 | | |
| meta-cymene | 66.98 | 65.93 | 65.72 | 64.84 | | |
| para-cymene | 27.85 | 23.73 | 25.37 | 12.32 | | |
| n-propyltoluene | 0.278 | 0.406 | 0.388 | 0.47 | | |
| other $C_{11}$ + aromatics | 0.02 | 0.120 | 0.0 | 0.33 | | |
| % ortho in cymenes | 4.50 | 4.47 | 4.77 | 3.75 | | |
| % meta in cymenes | 67.08 | 64.90 | 68.71 | 60.47 | | |
| % para in cymenes | 27.88 | 23.36 | 26.52 | 11.49 | | |
| % Conversion of: | | | | | | |
| ortho-cymene | — | 0.7 | 14.6 | 16.7 | 2.0 | 0.2 |
| meta-cymene | — | 3.2 | 7.5 | 9.8 | 10.4 | 1.7 |
| para-cymene | — | 16.2 | 57.7 | 58.8 | 62.3 | 14.6 |

The experimental results summarized above indicate that the ZSM-22 zeolite is para-selective in hydrocarbon conversion reactions.

It is to be understood that the foregoing is intended to be merely illustrative of certain specific embodiments of the disclosed invention. As those of skill in the art will readily appreciate, there are many variations which may be made on these specific embodiments without departing from the spirit of the invention described herein and such variations are clearly to be encompassed within the scope of the following claims.

What is claimed is:

1. A process for para-selective formation of substituted aromatic compounds comprising containing a feed comprised of one or more substituted aromatic compounds, under conversion conditions, with a ZSM-22 crystalline zeolite catalyst characterized by a silica to alumina mole ratio of at least about 20 and having an X-ray diffraction pattern of Table I, to yield a product in which the content of 1,4-disubstituted aromatic compounds is increased as compared to the content of said 1,4-disubstituted aromatic compounds in an equilibrium mixture of 1,2-disubstituted, 1,3-disubstitutd and 1,4-disubstituted aromatic compounds, wherein the substituted aromatic compound is a mono-substituted alkylbenzene.

2. A process of claim 1 wherein the alkyl substituent of the monosubstituted alkyl-benzene has 1 to 5 carbon atoms.

3. A process of claim 2 wherein the mono-substituted alkylbenzene is toluene, ethylbenzene, propylbenzene or butylbenzene.

4. A process of claim 3 wherein the mono-substituted alkylbenzene is toluene.

5. A process of claim 4 wherein the toluene is disproportionated to yield a product comprised of benzene and ortho-, meta-, and para-xylenes.

6. A process of claim 5 wherein the toluene is disproportionated at a temperature of about 500° C. and at about 2.8 liquid hourly space velocity.

7. A process of claim 1 wherein the feed further comprises an alkylating agent.

8. A process of claim 7 wherein the alkylating agent is selected from the group consisting of olefins having 2 to 12 carbon atoms, formaldehyde, alkyl halides, the alkyl portion of which has 1 to 16 carbon atoms, and alcohols, the alkyl portion of which has 1 to 16 carbon atoms.

9. A process of claim 8 wherein the alkyl substitutent of the mono-substituted alkylbenzene has 1 to 10 carbon atoms.

10. A process of claim 6 wherein the monosubstituted alkylbenzene is toluene, ethylbenzene, propylbenzene or butylbenzene.

11. A process of claim 8 wherein the mono-substituted alkylbenzene is toluene.

12. A process of claim 11 wherein the alkylating agent is methanol or ethylene.

13. A process of claim 12 wherein the alkylating agent is methanol.

14. A process of claim 12 wherein the reaction is conducted at a temperature of about 250° C. to about 750° C., at pressure of about 1 atmosphere, and at weight hourly space velocity of about 1 to about 1000.

15. A process of claim 14 wherein the product of the reaction comprises ortho-, meta- and para-xylenes with the amount of the para-xylenes exceeding the content thereof in the equilibrium mixture of the ortho-, meta- and para-xylenes.

16. A process of claim 12 wherein the alkylating agent is ethylene.

17. A process of claim 16 wherein the reaction is conducted at a temperature of about 250° C. to about 750° C., at pressure of about 1 atmosphere, and at weight hourly space velocity of about 1 to about 1000.

18. A process of claim 17 wherein the product of the reaction comprises 1-ethyl-2-methylbenzene, 1-ethyl-3-methylbenzene and 1-ethyl-4-methylbenzene with the amount of the 1-ethyl-4-methylbenzene exceeding to the content thereof in the equilibrium mixture of the 1-ethyl-2-methylbenzene, 1-ethyl-3-methylbenzene and 1-ethyl-4-methylbenzene.

19. A process for selective reaction of a para-disubstituted aromatic compound, said process comprising contacting a feed comprised of two or more disubstituted aromatic compounds, under conversion conditions, with a ZSM-22 crystalline zeolite catalyst characterized by a silica to alumina mole ratio of at least about 20 and having an X-ray diffraction pattern of Table I, to selectively dealkylate or transalkylate the para-disubstituted compound and yield a product in which the content of the para-disubstituted aromatic compound is reduced relative to the content of the para-disubstituted compound in the feed prior to said contacting.

20. A process of claim 19 wherein the disubstituted aromatic compounds are dialkyl substituted benzenes.

21. A process of claim 20 wherein two alkyl substitutents of the dialkyl substituted benzenes are the same or different and each alkyl substitutent has 1 to 10 carbon atoms.

22. A process of claim 21 wherein the feed comprises 1,3- and 1,4-disubstituted aromatic compounds.

23. A process of claim 22 wherein the disubstituted aromatic compounds are 1-isopropyl-3-methylbenzene (meta-cymene) and 1-isopropyl-4-methylbenzene (para-cymene).

24. A process of claim 23 whereint e para-cymene is selectively dealkylated to a greater extent than the meta-cymene.

25. A process of claims 23 or 24 wherein the reaction is conducted at a temperature of about 150° C. to about 800° C., a pressure of about 0.1 to about 100 atmospheres, and a feed weight hourly space velocity of about 0.1 to about 100.

* * * * *

UNITED STATES PATENT AND TRADEMARK OFFICE
CERTIFICATE OF CORRECTION

PATENT NO. : 5,248,841
DATED : September 28, 1993
INVENTOR(S) : L.B. Young

It is certified that error appears in the above-identified patent and that said Letters Patent is hereby corrected as shown below:

Col. 17, claim 1, line 34, change "containing" to --contacting--.

Col. 18, claim 10, line 24, change "6" to --9--.

Col. 18, claim 11, line 27, change "8" to --10--.

Col. 18, claim 14 line 33, change "12" to --13--.

Col. 18, claim 18, line 51, delete "to".

Col. 20, claim 24, line 3, delete "whereint e" and insert --wherein the--.

Signed and Sealed this

Twenty-ninth Day of March, 1994

Attest:

BRUCE LEHMAN

Attesting Officer     Commissioner of Patents and Trademarks